United States Patent
Yao et al.

(10) Patent No.: US 9,522,125 B1
(45) Date of Patent: Dec. 20, 2016

(54) METHOD OF TREATING CANCER

(71) Applicant: Macau University of Science and Technology, Macau (CN)

(72) Inventors: Xiao-Jun Yao, Macau (CN); Lai-Han Leung, Macau (CN); Lian-Xiang Luo, Macau (CN); Wen-Luan Hsiao, Macau (CN); Liang Liu, Macau (CN)

(73) Assignee: Macau University of Science and Technology, Macau (CN)

( * ) Notice: Subject to any disclaimer, the term of this patent is extended or adjusted under 35 U.S.C. 154(b) by 0 days.

(21) Appl. No.: 14/945,436

(22) Filed: Nov. 19, 2015

Related U.S. Application Data

(60) Provisional application No. 62/203,388, filed on Aug. 10, 2015.

(51) Int. Cl.
*A61K 31/136* (2006.01)

(52) U.S. Cl.
CPC .................................. *A61K 31/136* (2013.01)

(58) Field of Classification Search
None
See application file for complete search history.

(56) References Cited

PUBLICATIONS van Breukelen et al. In European Journal of Cancer 27(12):1627-1629 (1991).*
Suga et al. in Japanese Journal of Oncology 16(2): 147-151 (1986) (Abstract).*
Scaggliotti et al. in European Journal of Cancer 48, 961-973 (2012).*
Ross Camidge et al. in Lancet Oncology 13, 1011-1019 (2012).*
Solomon et al. Journal of Clinical Oncology 33(9):972-974 (2015).*
Parker et al. in Lancet 376(9757): 2009-2017 (2010).*
Silver et al in Journal of Clinical Oncology 9(5):754 761 (1991) (Abstract).*
Landys et al. In Investigational New Drugs 3, 133-137 (1985).*
Bergethon et al. in Journal of Clinical Oncology 30(8):863-870 (2012).*
Fox, E.J. in Neurology 63(Suppl 6), S15-S18 (2004).*
A. Jemal, R. Siegel, E Ward, et al., "Cancer statistics, 2009," CA Cancer J Clin, vol. 59, No. 4, pp. 225-249, 2009.
M. Alamgeer, V. Ganju,and D.N. Watkins, "Novel therapeutic targets in non-small cell lung cancer," Curr Opin Pharmacol, vol. 13, No. 3, pp. 394-401, 2013.
Z. Wang, Z. Shen, Z. Li, et al., "Activation of the BMP-BMPR pathway conferred resistance to EGFR-TKIs in lung squamous cell carcinoma patients with EGFR mutations," Proc Natl Acad Sci U S A, vol. No. pp. 2015.
M. Soda, Y.L. Choi, M. Enomoto, et al., "Identification of the transforming EML4-ALK fusion gene in non-small-cell lung cancer," Nature, vol. 448, No. 7153, pp. 561-566, 2007.
K.D. Davies, A.T. Le, M.F. Theodoro, et al., "Identifying and targeting ROS1 gene fusions in non-small cell lung cancer," Clin Cancer Res, vol. 18, No. 17, pp. 4570-4579, 2012.
M.R. Junttila, A.N. Karnezis, D. Garcia, et al., "Selective activation of p53-mediated tumour suppression in high-grade tumours," Nature, vol. 468, No. 7323, pp. 567-571, 2010.
W. Zhou, D. Ercan, L. Chen, et al., "Novel mutant-selective EGFR kinase inhibitors against EGFR T790M," Nature, vol. 462, No. 7276, pp. 1070-1074, 2009.
H.R. Kim, S.M. Lim, H.J. Kim, et al., "The frequency and impact of ROS1 rearrangement on clinical outcomes in never smokers with lung adenocarcinoma," Ann Oncol, vol. 24, No. 9, pp. 2364-2370, 2013.
A.T. Shaw, S.H. Ou, Y.J. Bang, et al., "Crizotinib in ROS1-rearranged non-small-cell lung cancer," N Engl J Med, vol. 371, No. 21, pp. 1963-1971, 2014.
M.M. Awad, R. Katayama, M. McTigue, et al., "Acquired resistance to crizotinib from a mutation in CD74-ROS1," N Engl J Med, vol. 368, No. 25, pp. 2395-2401, 2013.
R.C. Doebele, A.B. Pilling, D.L. Aisner, et al., "Mechanisms of resistance to crizotinib in patients with ALK gene rearranged non-small cell lung cancer," Clin Cancer Res, vol. 18, No. 5, pp. 1472-1482, 2012.
H.Y. Zou, Q. Li, L.D. Engstrom, et al., "PF-06463922 is a potent and selective next-generation ROS1/ALK inhibitor capable of blocking crizotinib-resistant ROS1 mutations," Proc Natl Acad Sci U S A, vol. 112, No. 11, pp. 3493-3498, 2015.
R.S. Nickel, F. Keller, J. Bergsagel, et al., "Mitoxantrone as a substitute for daunorubicin during induction in newly liagnosed lymphoblastic leukemia and lymphoma," Pediatr Blood Cancer, vol. 61, No. 5, pp. 810-814, 2014.
E. Guerrero, A. Sorice, F. Capone, et al., "Vitamin C effect on mitoxantrone-induced cytotoxicity in human breast cancer cell lines," PLoS One, vol. 9, No. 12, pp. e115287, 2014.
P.L. Zinzani, M. Tani, S. Fanti, et al., "A phase 2 trial of fludarabine and mitoxantrone chemotherapy followed by yttrium-90 ibritumomab tiuxetan for patients with previously untreated, indolent, nonfollicular, non-Hodgkin lymphoma," Cancer, vol. 112, No. 4, pp. 856-862, 2008.

* cited by examiner

*Primary Examiner* — Dennis Heyer
(74) *Attorney, Agent, or Firm* — Eagle IP Limited; Jacqueline C. Lui

(57) ABSTRACT

The present invention discloses that a method of treating cancer, preferably non-small cell lung cancer, comprises administrating mitoxantrone. The present invention also discloses a method of inhibiting ROS1 kinase comprising administrating mitoxantrone. A pharmaceutical composition comprising mitoxantrone is also disclosed.

6 Claims, 10 Drawing Sheets
(7 of 10 Drawing Sheet(s) Filed in Color)

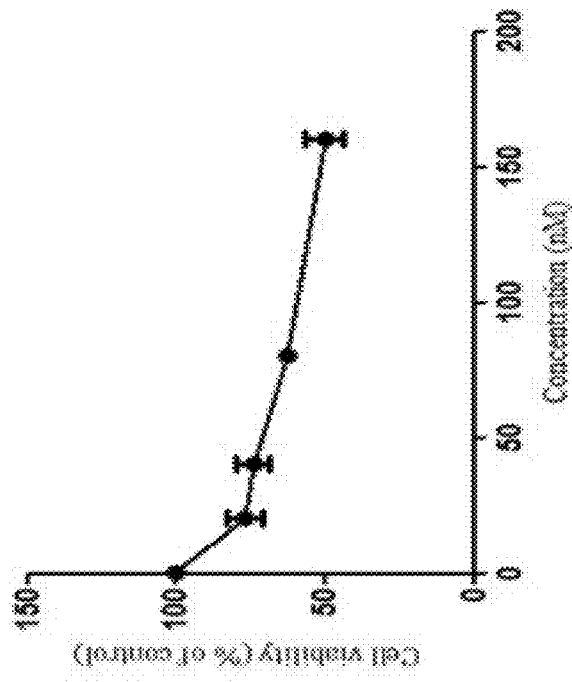
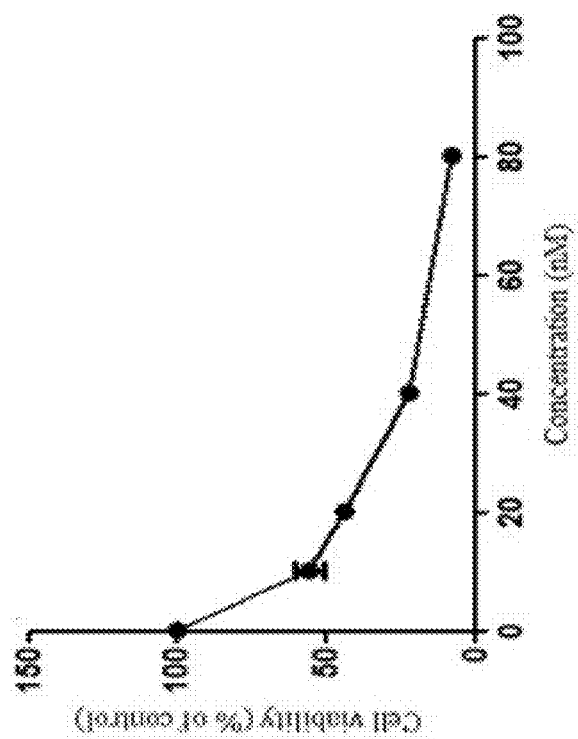
Fig.3A
Fig.3B

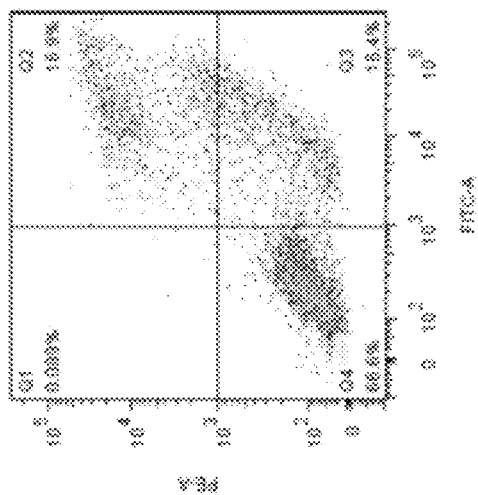
Fig.5C Mitoxantrone (5nM)
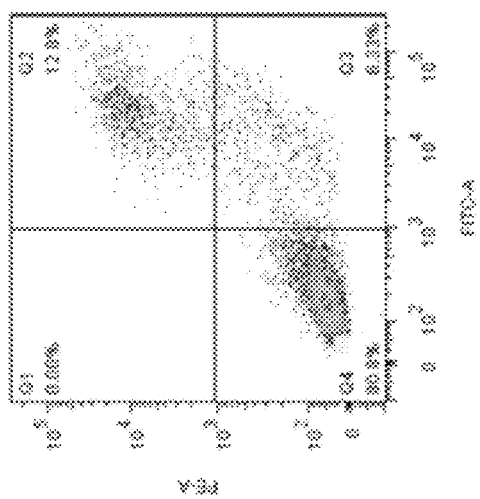
Fig.5B Control
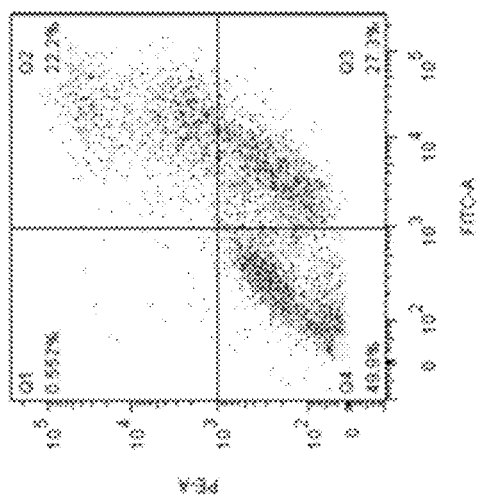
Fig.5A Crizotinib (2.5μM)

METHOD OF TREATING CANCER

CROSS-REFERENCE TO RELATED APPLICATION

This application claims benefit under 35 U.S.C. §119(e) of U.S. Provisional Application having Ser. No. 62/203,388 filed on 10 Aug. 2015, which is hereby incorporated by reference herein in its entirety.

FIELD OF INVENTION

This invention relates to a ROS1 kinase inhibitor and its use in treating cancer, in particular non-small cell lung cancer. This invention also relates to a pharmaceutical composition comprising the ROS1 kinase inhibitor.

BACKGROUND OF INVENTION

Lung cancer is one of the most prevalent malignancies and remains a leading cause of cancer-related death for both men and women worldwide. Non-small cell lung cancer (NSCLC) is the most common form of lung cancer, which accounts for approximately 85% of all lung cancer cases.

SUMMARY OF INVENTION

One example embodiment is a method of treating cancer, which includes administrating a pharmaceutically effective amount of mitoxantrone to a subject in need thereof. The tumors of the cancer express ROS1 fusion gene.

Another example embodiment is a pharmaceutical composition for treating cancer whose tumors express ROS1 fusion gene. The pharmaceutical composition includes mitoxantrone and a pharmaceutically acceptable carrier.

A further example embodiment is a method of inhibiting ROS1 kinase that includes administrating a pharmaceutically effective amount of mitoxantrone to a subject in need thereof.

BRIEF DESCRIPTION OF FIGURES

The patent or application file contains at least one drawing executed in color. Copies of this patent or patent application publication with color drawing(s) will be provided by the Office upon request and payment of the necessary fee.

FIG. 3A shows the cell viability of HCC78 cells treated by mitoxantrone for 72 h by MTT assay. FIG. 3B shows the cell viability of lung normal cells CCD19-Lu treated by mitoxantrone for 72 h by MTT assay.

FIG. 5A, FIG. 5B, FIG. 5C, FIG. 5D, FIG. 5E and FIG. 5F show the flow cytometry analysis of HCC78 cells treated by 2.5 µM crizotinib and mitoxantrone with the concentrations of 5 nM, 10 nM and 20 nM.

DETAILED DESCRIPTION OF THE PREFERRED EMBODIMENTS

As used herein and in the claims, "comprising" means including the following elements but not excluding others.

NSCLC is heterogeneous disease characterized by driver oncogenic alterations that can be targeted through precision tyrosine kinase inhibitors (TKIs). The most prevalent mutated or rearranged oncogenes identified in NSCLCs are KRAS (V-Ki-ras2 Kirsten rat sarcoma viral oncogene homolog), epidermal growth factor receptor (EGFR), anaplastic lymphoma kinase (ALK) and c-ros oncogene 1 (ROS1) etc. ROS1 encodes a receptor tyrosine kinase of the insulin receptor super family with no known ligand and little known about its normal function. The prevalence of ROS1 rearrangement in NSCLC is estimated at 1-2%. Crizotinib is the only current clinically-available, orally available, ATP-competitive small molecule inhibitor of ALK/ROS1 with potency against ROS1 kinase, which displays marked anti-tumor activity both in vitro and in vivo as well as in clinics. Although most patients with ROS1 fusion-driven NSCLC derive remarkable benefit from crizotinib, durable responses to crizotinib therapy lead to the development of eventual drug resistance, a common feature similar to other TKI drugs. Therefore, development of other novel ROS1 kinase inhibitors is essential to treat NSCLC with ROS1 gene fusion.

Figure 1:
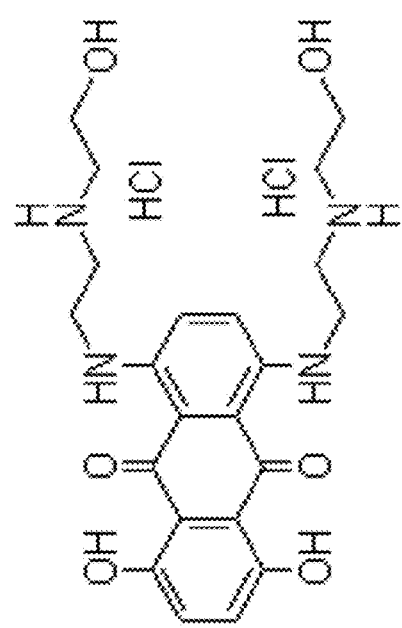
FIG. 1 shows the chemical structure of mitoxantrone.

The inventors applied a NSCLC cell line HCC78 harboring the SCL34A2-ROS1 fusion gene, and identified mitoxantrone as a new potent ROS1 kinase inhibitor. In this study, the inventors found out that Mitoxantrone can directly inhibit ROS1 kinase activity and suppress the phosphorylation of ROS1 as well as its downstream anti-apoptotic and growth signaling. In this study, the inventors also have found the new role and function of mitoxantrone by directly targeting ROS1 kinase, which is potentially useful to be developed as new ROS1 kinase inhibitor to treat lung cancer, in particular non-small cell lung cancer. The chemical structure of mitoxantrone was shown in FIG. 1.

1. Material and Methods 1.1 Cell Culture and Reagents

HCC78 cell line was purchased from the American Type Culture Collection (ATCC) (Manassas, Va., USA). Cells were cultured in RPMI-1640 medium containing 10% fetal bovine serum (FBS), 100 units/mL penicillin, and 100 µg/mL streptomycin under a humidified atmosphere of 5% $CO_2$ at 37° C. Mitoxantrone was dissolved in DMSO.

1.2 In Vitro ROS1 Enzymatic Assay

LanthaScreen® Eu kinase binding assay was used to determine the changes in kinase activity, which is an assay based on the binding and displacement property of the kinase with substrate. Briefly, the assay was performed at room temperature for 1 hour in a total volume of 15 µL, including 5 µL of test compound, 5 µL of kinase/antibody mixture and 5 µL of tracer. The signal of the 384-well plate was then measured at the end of the reactions. Emission ratio was calculated by dividing the acceptor/tracer emission signal (665 nM) by the antibody/donor emission signal (615 nM).

1.3 MTT Cytotoxicity Assay 3000 cells were seeded on 96-well plates, then the plates were cultured overnight for cell adhesion, and treated with DMSO or various concentrations of mitoxantrone for 72 h.

10 μL of MTT (5 mg/mL; Sigma) was added in each well, and incubation was continued for another 4 hours, then the dark blue crystals were dissolved in 100 μL resolved solution (10% SDS and 0.1 mM HCL). Finally, the absorbance was measured at 570 nm by a microplate reader (Tecan, Morrisville, N.C., USA). The cell viability was calculated relative to untreated controls, and results were presented based on at least 3 independent experiments.

1.4 Apoptosis Analysis

HCC78 cells were seeded on a 6-well plate, and were allowed to attach overnight. The cells were treated with a dilution series of mitoxantrone for 48 h, collected by trypsin and washed twice with ice-cold PBS, and then resuspended in 100 μl 1× binding buffer. 2 μL Annexin-V FITC and 4 μL PI (100 μg/ml) were added to the solution and mixed well. After incubation for 15 min in the dark at room temperature, 400 μL of 1× binding buffer was added to each tube, where apoptosis level was then quantitatively analyzed using a FACSAria III Flow Cytometer (BD Biosciences, San Jose, Calif., USA).

1.5 Western Blot Analysis

After cells were plated on 6-well plates overnight, a wide concentrations of mitoxantrone were administered for 48 h. Cells were washed twice with cold PBS and then lysed in RIPA lysis buffer containing protease and phosphatase inhibitors, and protein concentration of the cell lysates were measured using the Bio-Rad protein Assay kit (Bio-Rad, Philadelphia, Pa., USA). After equalizing the protein concentrations of the samples, 5× laemmli buffer was added and boiled at 100° C. for 5 min. Equal amounts of protein samples (30 μg) were subjected to SDS-PAGE and separated with a 10% gel; then the separated proteins were transferred to a Nitrocellulose (NC) membrane, which was then exposed to 5% non-fat dried milk in TBS containing 0.1% Tween 20 (0.1% TBST) for 1 h at room temperature, followed by overnight incubation at 4° C. with primary anti-bodies (1:1000 dilutions). After being washed 3 times by TBST, the membranes were incubated with secondary fluorescent antibodies (1:10000 dilutions) to rabbit or mouse, the signal intensity of the membranes was detected by an LI-COR Odessy scanner (Belfast, Me., USA). Antibodies against GAPDH, p-AKT, p-ROS1, ROS1, p-ERK, ERK, p-STAT3, STAT3 were purchased from Cell signaling Technology. Anti-AKT antibody was acquired from Santa Cruz Biotechnology.

1.6 Molecular Docking

Molecular docking calculation is performed to study the binding mode of mitoxantrone to ROS1 kinase by using Induced Fit docking module in Schrodinger software (Schrodinger, Inc., New York, N.Y., 2009). The structure of mitoxantrone is prepared and optimized in the LigPrep module. The 3D structure of ROS1 kinase is derived from the PDB database (PDB ID: 3ZBF) and prepared using the Protein Preparation Wizard. In the molecular docking calculation, crizotinib is used to define the active site. The binding pose of ligand is evaluated with XP docking score. The pose with the best score is selected for further analysis.

1.7 Statistical Analysis

Statistical analysis was conducted using Graph Prim5.0. Difference between datasets was assessed using on-way ANVOA. P<0.05 was considered statistically significant.

2. Results 2.1 ROS1 Enzymatic Assay

By performing biochemical enzymatic assays, mitoxantrone was shown in the Table 1 to be an ATP-competitive inhibitor of ROS1 with $IC_{50}$ value of 36.03 nM, while the $IC_{50}$ value of the control drug crizotinib is 52.76 nM, indicating that mitoxantrone is even more effective in inhibiting ROS1 kinase than the current clinically-applied drug crizotinib.

TABLE 1

The IC50 value of crizotinib and mitoxantrone

| Drugs | $IC_{50}$ (nM) |
|---|---|
| Crizotinib | 52.76 |
| Mitoxantrone | 36.03 |

Figure 2A:
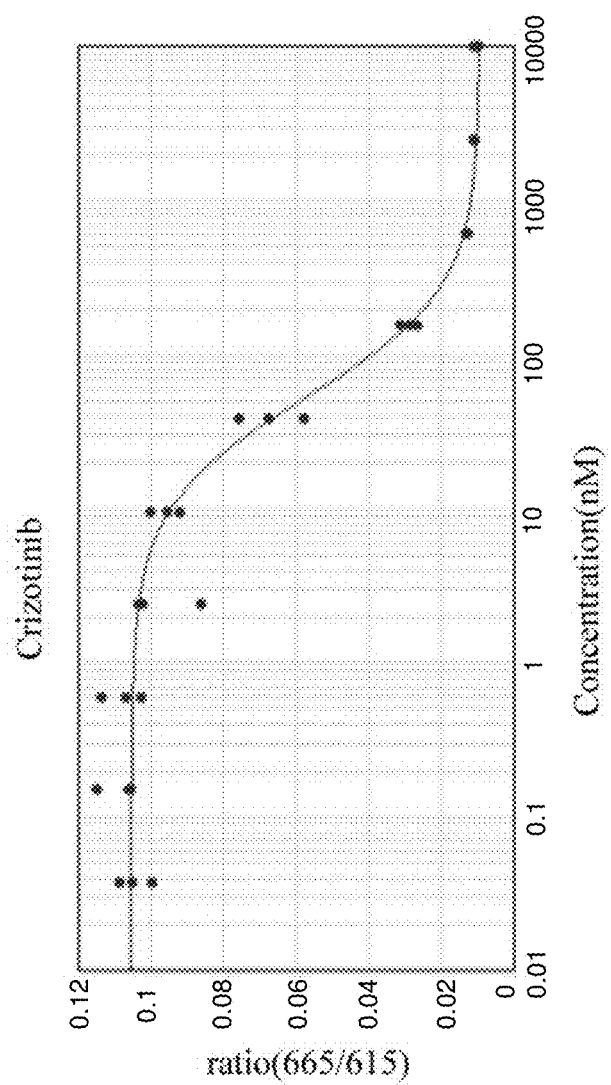
FIG. 2A and FIG. 2B show the kinase activity assay of mitoxantrone on HCC78, and Crizotinib was used as positive control drug to demonstrate positive ROS kinase inhibition ability.
Figure 2B:
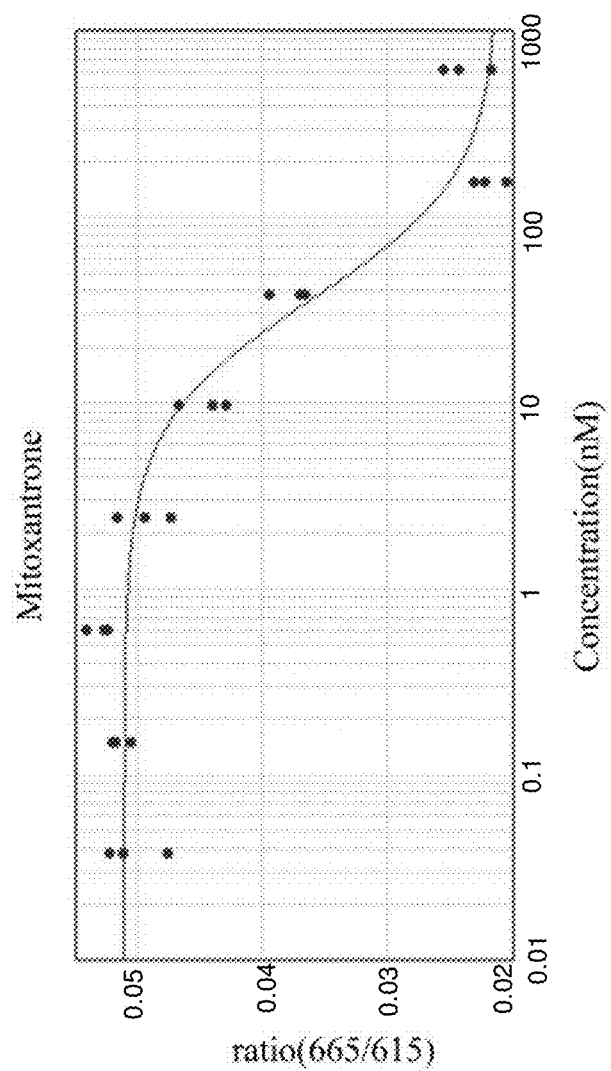

The kinase activity assay of mitoxantrone on HCC78 was shown in FIG. 2A, and Crizotinib was used as positive control drug to demonstrate positive ROS kinase inhibition ability as shown in FIG. 2B.

2.2 Cytotoxicity Effect of Mitoxantrone on HCC78 NSCLC Cells (With ROS1 Fusion Gene) and Normal Lung Cells (CCD19-Lu)

MTT assay showed that mitoxantrone has an inhibition activity against HCC78 cell. The cell viability of HCC78 cells treated by mitoxantrone for 72 h is shown in FIG. 3A and that of normal lung cell CCD19-Lu for 72 h treatment by mitoxantrone is shown in FIG. 3B. As shown in Table 2, the $IC_{50}$ of mitoxantrone on HCC78 is 13.83±2.49 nM, while a lower cytotoxicity on normal lung cells (CCD19-Lu) was shown after 72 h treatment. The $IC_{50}$ in CCD19-Lu is higher than 160 nM, which is at least 11.6 fold than that on HCC78.

TABLE 2

The $IC_{50}$ values of mitoxantrone on HCC78 cells and CCD19-Lu cells

| Cell line | $IC_{50}$ value (nM) |
|---|---|
| HCC78 | 13.83 ± 2.49 |
| CCD19-Lu | >160 |

2.3 Mitoxantrone Significantly Induced Apoptosis in HCC78 Cells

Figure 4:
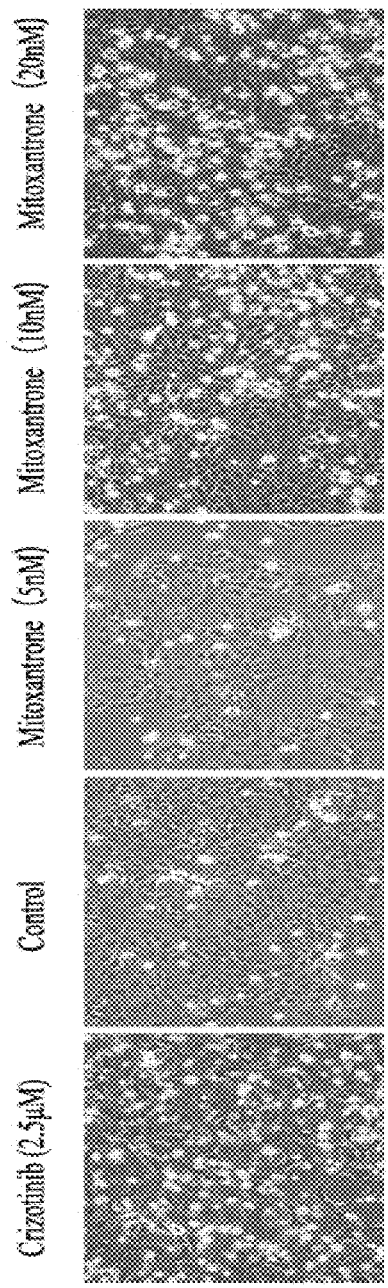
FIG. 4 shows the morphology of HCC78 cells treated by 2.5 µM crizotinib and mitoxantrone with the concentrations of 5 nM, 10 nM and 20 nM.
Figure 5F:
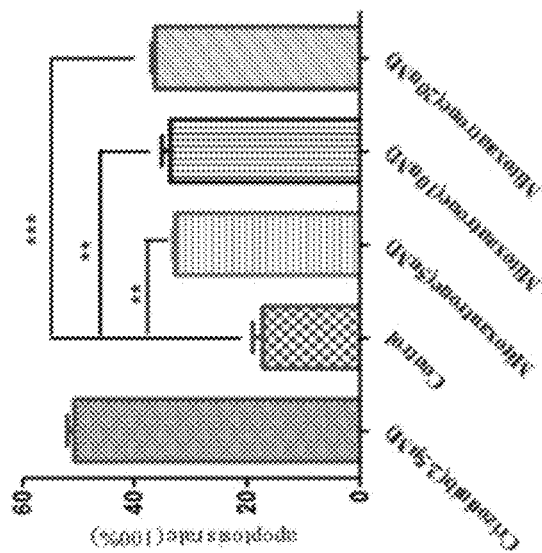
Figure 5E:
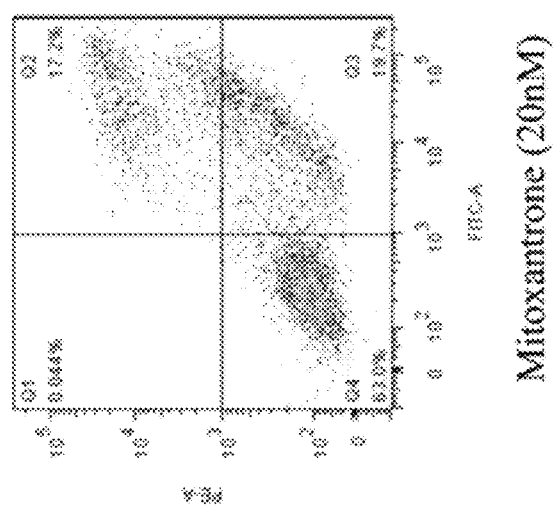
Figure 5D:
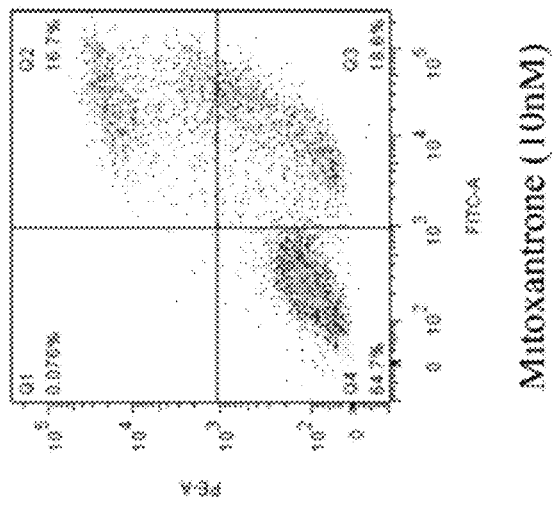

When HCC78 cells were treated with mitoxantrone, cells detached and became smaller starting at 10 nM treatment as shown in FIG. 4, which is a morphological indication of apoptosis. Next, by using a more quantitative apoptosis measurement method, the flow cytometry analysis in FIGS. 5A-5F showed that mitoxantrone exhibits anticancer ability through induction of apoptosis on HCC78 cells in a concentration-dependent manner. Treatment on HCC78 cells with mitoxantrone induced significant apoptosis levels when compared with the control group.

Figure 6:
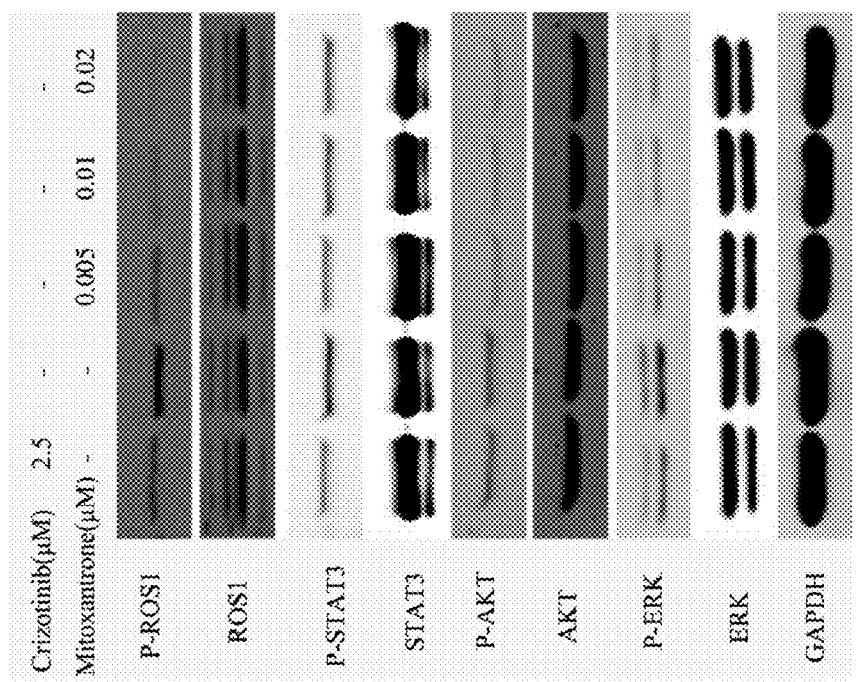
FIG. 6 shows the western blot analysis of HCC78 cells treated by 2.5 µM crizotinib and mitoxantrone with the concentrations of 5 nM, 10 nM and 20 nM.

2.4 Mitoxantrone LED to a Dose-Dependent Suppression of ROS1 Phosphorylation as Well as its Downstream Anti-Apoptotic and Growth Signaling As shown in FIG. 6, treatment of HCC78 cells with mitoxantrone led to a dose-dependent decrease of ROS1 phosphorylation as well as its downstream signaling molecules Erk1/2, STAT3 and AKT signaling, further supporting the anti-cancer effect of mitoxantrone and elucidating its treatment mechanism. Crizotinib was included as positive control.

2.5 Binding Mode Between Mitoxantrone and ROS1 Kinase.

Figure 7A:
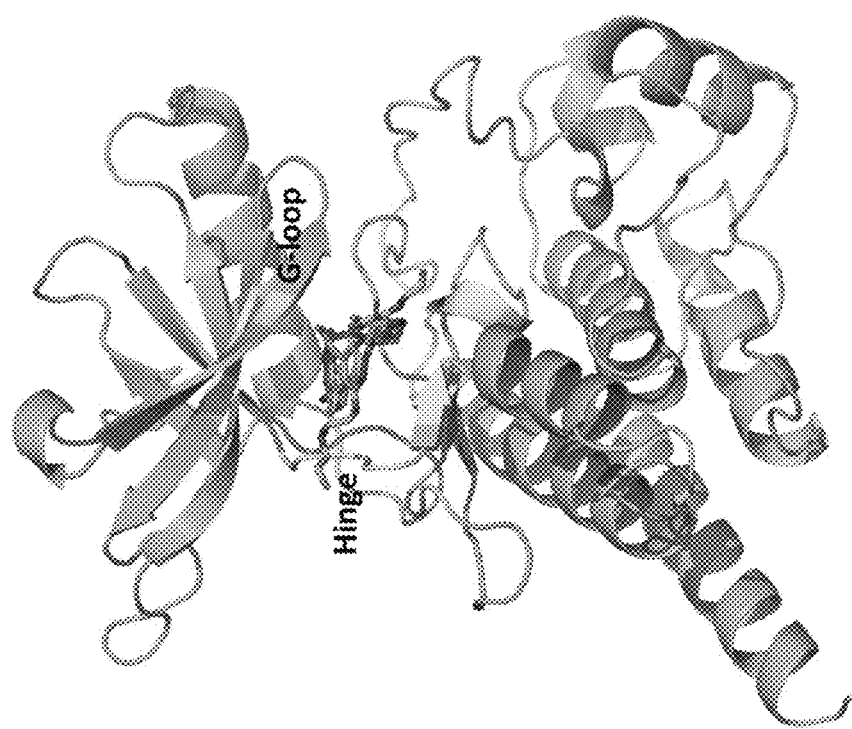
FIG. 7A and FIG. 7B illustrate the interaction between residues on ROS1 kinase and mitoxantrone by molecular docking calculations.
Figure 7B:
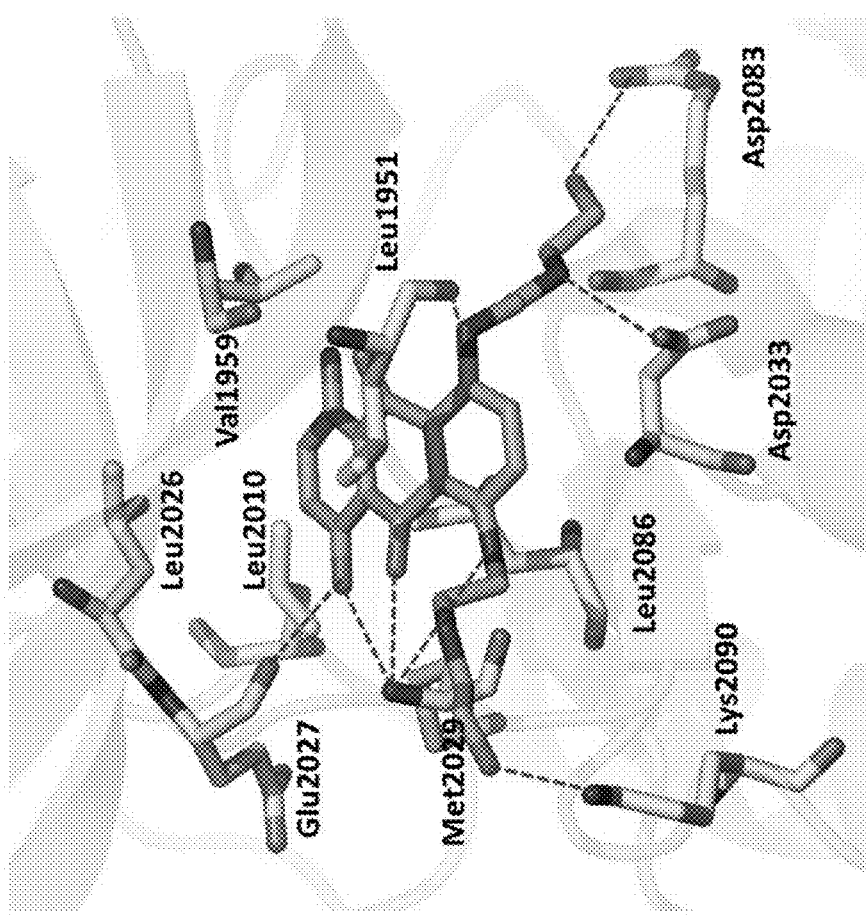

Molecular docking calculations prove that mitoxantrone and crizotinib have similar binding mode with ROS1 kinase. The docking scores of mitoxantrone and crizotinib to ROS1 kinase are −13.582 and −9.674 Kcal/mol, respectively. Mitoxantrone is shown to have a better binding affinity to ROS1 kinase than crizotinib. This is consistent with the results from both MTT and enzyme inhibition activity. FIG. 7A shows the n between crizotinib and ROS1 kinase. As observed in FIG. 7A and FIG. 7B, the anthracenedione scaffold of mitoxantrone overlapped well with the core structure of crizotinib. As further illustrated in FIG. 7B, residues Leu1951, Glu2027, Met2029, Asp2033, Asp2083, Lys2090 of the ROS1 kinase had hydrogen bond interaction with mitoxantrone as shown by broken lines in red. Residues Glu2027 and Met2029 in the hinge region formed multiple hydrogen bonds with the polar atoms of anthracenedione part, while residues Leu1951, Asp2033, Asp2083 and Lys2090 had hydrogen bonds with the two substituted "tails". Other residues, such as Val1959, Leu2012, Leu2026, Leu2086, also had hydrophobic interaction with mitoxantrone.

The exemplary embodiments of the present invention are thus fully described. Although the description referred to particular embodiments, it will be clear to one skilled in the art that the present invention may be practiced with variation of these specific details. Hence this invention should not be construed as limited to the embodiments set forth herein.

What is claimed is:

1. A method of treating lung cancer in a subject in need thereof, comprising:
    administering a pharmaceutically effective amount of mitoxantrone to the subject to treat the lung cancer, wherein tumors of the lung cancer express ROS1 fusion gene.

2. The method of claim 1, wherein the lung cancer is non-small cell lung cancer.

3. The method of claim 1, wherein the mitoxantrone inhibits ROS1 kinase.

4. A method of treating lung cancer by inhibiting ROS1 kinase in a subject in need thereof, comprising:
    administering a pharmaceutically effective amount of mitoxantrone to the subject to treat the lung cancer by inhibiting the ROS1 kinase.

5. The method of claim 4, wherein the lung cancer is non-small cell lung cancer.

6. The method of claim 4, wherein tumors of the lung cancer express ROS1 fusion gene.

* * * * *